(12) United States Patent
Butler et al.

(10) Patent No.: US 9,095,386 B2
(45) Date of Patent: Aug. 4, 2015

(54) SPINAL ROD GUIDE FOR A VERTEBRAL SCREW SPINAL ROD CONNECTOR ASSEMBLY

(75) Inventors: Michael S. Butler, St. Charles, IL (US); Brian D. Hartsell, Aurora, IL (US); Thomas J. Wegrzyn, III, Chicago, IL (US)

(73) Assignee: Life Spine, Inc., Huntley, IL (US)

(*) Notice: Subject to any disclaimer, the term of this patent is extended or adjusted under 35 U.S.C. 154(b) by 291 days.

(21) Appl. No.: 12/408,684

(22) Filed: Mar. 21, 2009

(65) Prior Publication Data

US 2009/0240292 A1 Sep. 24, 2009

Related U.S. Application Data

(60) Provisional application No. 61/070,290, filed on Mar. 21, 2008.

(51) Int. Cl.
*A61B 17/70* (2006.01)

(52) U.S. Cl.
CPC ......... *A61B 17/7091* (2013.01); *A61B 17/7085* (2013.01); *A61B 17/7083* (2013.01)

(58) Field of Classification Search
CPC ................................. A61B 17/7083–17/7091
USPC ........................................................ 606/86 A
See application file for complete search history.

(56) References Cited

U.S. PATENT DOCUMENTS

| | | | |
|---|---|---|---|
| 5,882,350 | A | 3/1999 | Ralph et al. |
| 6,074,391 | A | 6/2000 | Metz-Stavenhagen et al. |

(Continued)

FOREIGN PATENT DOCUMENTS

| | | | |
|---|---|---|---|
| WO | WO-2006/091863 A2 | | 8/2006 |
| WO | WO 2006091863 A2 | * | 8/2006 |
| WO | WO 2007/149426 A2 | | 12/2007 |

OTHER PUBLICATIONS

International Search Report and Written Opinion for PCT/US20019/037905, mail date May 12, 2009, 6 pages.

*Primary Examiner* — Jerry Cumberledge
*Assistant Examiner* — Nicholas Plionis
(74) *Attorney, Agent, or Firm* — Foley & Lardner LLP

(57) ABSTRACT

A spinal rod guide and/or guide assembly is provided for mounting a spinal rod onto a spinal rod holder/connector of a vertebral bone screw. The spinal rod guide is configured to extend between an opening in a patient's body and the spinal rod holder of the vertebral bone screw assembly, to receive a spinal rod therein, and thereafter accurately guide the spinal rod into the spinal rod holder. The spinal rod guide is defined by a first elongated arc portion and a second elongated arc portion to define a guide tube for the introduction and placement of additional spinal rod components onto the spinal rod connector, particularly, but not necessarily, for securing the spinal rod into the spinal rod connector. The elongated arc portions are mountable or initially attached onto a top of a spinal rod holder of a spinal rod bone screw assembly. The elongated arc portions (tube) define first and second longitudinal slots extending from a top of the elongated arc portions to a bottom of the elongated arc portions. The two longitudinal slots are situated such as to be diametrically opposite one another. Each longitudinal slot aligns with a spinal rod slot of the spinal rod holder to thereby allow easy placement of the spinal rod into the spinal rod holder. Thereafter, the defined elongated tube provides direct communication and alignment with the top of the spinal rod holder in order to receive a spinal rod connector drive screw for securing the spinal rod into the spinal rod holder.

23 Claims, 3 Drawing Sheets

(56) References Cited

U.S. PATENT DOCUMENTS

| | | |
|---|---|---|
| 6,248,104 B1 | 6/2001 | Chopin et al. |
| 2004/0138662 A1* | 7/2004 | Landry et al. ............... 606/61 |
| 2005/0131408 A1* | 6/2005 | Sicvol et al. ............... 606/61 |
| 2005/0192579 A1* | 9/2005 | Jackson ...................... 606/72 |
| 2006/0271050 A1* | 11/2006 | Piza Vallespir ............. 606/61 |
| 2006/0276792 A1* | 12/2006 | Ensign et al. ............... 606/61 |
| 2007/0179502 A1* | 8/2007 | Raynor et al. .............. 606/61 |
| 2007/0191836 A1* | 8/2007 | Justis ......................... 606/61 |
| 2007/0191840 A1 | 8/2007 | Pond, Jr. et al. |
| 2007/0270867 A1 | 11/2007 | Miller et al. |
| 2008/0009864 A1 | 1/2008 | Forton et al. |
| 2008/0051794 A1* | 2/2008 | Dec et al. ................... 606/73 |
| 2008/0114403 A1* | 5/2008 | Kuester et al. ............. 606/308 |
| 2008/0119849 A1 | 5/2008 | Beardsley et al. |
| 2008/0228228 A1 | 9/2008 | Hestad et al. |
| 2010/0228090 A1 | 9/2010 | Weisenburgh et al. |

* cited by examiner

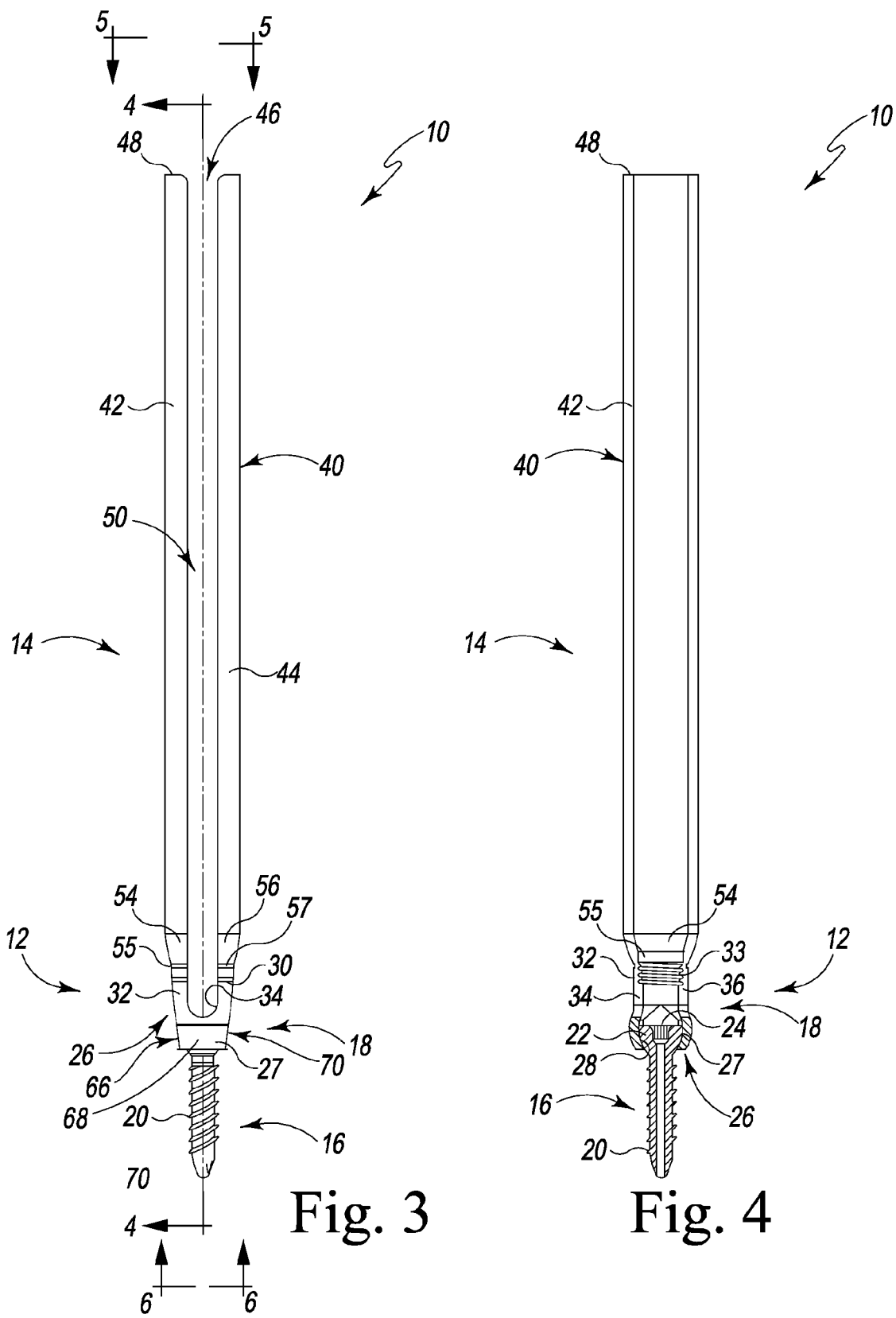

SPINAL ROD GUIDE FOR A VERTEBRAL SCREW SPINAL ROD CONNECTOR ASSEMBLY

RELATED APPLICATIONS

This patent application claims the benefit of and/or priority to U.S. Provisional Patent Application Ser. No. 61/070,290 filed Mar. 21, 2008, entitled "Spinal Rod Guide For A Vertebral Screw Spinal Rod Connector Assembly" the entire contents of which is specifically incorporated herein by this reference.

BACKGROUND OF THE INVENTION

1. Field of the Invention

The present invention relates to spine fixation components, constructs and assemblies and, more particularly, to a construct for the implantation of a spinal rod.

2. Background Information

Spinal orthopedic assemblies and constructs such as spine plates, spinal bone screw assemblies for spinal rods and other devices (spinal components) have made a profound contribution to the correction of spinal deformities, accidents and other problems in the thoracic, lumbar and sacral spine. These and other spinal devices are fixed to vertebrae using vertebral bone screws. Vertebral bone screws are specially designed and manufactured bone screws that are placed into the bone of a vertebra. One typical placement of a bone screw for the fixation of a spinal component is through a pedicle of the vertebral body. Vertebral bone screws placed in this manner offer superior strength and pull-out resistance as compared to other forms of fixation in spine surgery. The ability to achieve pedicle fixation has allowed surgeons to obtain more secure fixation of the involved vertebral segments, which permits more powerful correction of spine problems and reported better clinical outcomes. Vertebral bone screws for pedicle fixation are typically known as pedicle screws.

Of the various spinal components, spinal rods are used in certain circumstances to fix a number of vertebrae in a particular orientation. As such, spinal rods must be fixed to the vertebrae. The pedicle screw provides a solid foundation for the attachment of a spinal rod. In one form, a spinal rod may be held relative to a pedicle screw by a spinal rod connector that is coupled to the pedicle screw. The spinal rod connector is typically rotationally connected to the pedicle screw in order to allow various connection orientations of the spinal rod relative to the longitudinal axis of the pedicle screw. The spinal rod connector includes features that allow the reception and capture of the spinal rod. This is accomplished by placing the spinal rod through an opening in the body via which the pedicle screw and spinal rod connector is attached to the vertebra. The spinal rod is then placed through the body opening and directed into and oriented on the spinal rod connector. Thereafter, the spinal rod must be secured to each individual spinal rod connector. This is typically accomplished by installing a spinal rod connector screw onto the spinal rod connector via a tube temporarily connected to the spinal rod connector. Because of this complicated procedure, it is fairly difficult and/or cumbersome to situate and mount a spinal rod onto a spinal rod connector of a vertebral bone screw.

In view of the above, it is clear that there is a need for a better manner of mounting a spinal rod onto a spinal rod connector of a vertebral bone screw.

SUMMARY OF THE INVENTION

The present invention is a spinal rod guide for mounting a spinal rod onto a spinal rod holder of a vertebral bone screw, particularly, but not necessarily, for use in minimally invasive surgery. The spinal rod guide is configured to extend between an opening in a patient's body and the spinal rod holder of the vertebral bone screw, to receive a spinal rod therein, and thereafter accurately guide the spinal rod into the spinal rod holder. The spinal rod guide is defined by a first elongated arc portion and a second elongated arc portion that together define a first elongated slot and a second elongated slot sized for the introduction and placement of the spinal rod into the spinal rod holder.

The first and second elongated arc portions together define an elongated tube that allows additional spinal rod components to be guided and placed into/onto the spinal rod connector, particularly, but not necessarily, for securing the spinal rod into the spinal rod holder.

An embodiment of the spinal rod guide comprises a first elongated arc portion that is attachable to a spine rod holder of a spinal rod bone screw assembly and a second elongated arc portion that is attachable to the spine rod holder of the spinal rod bone screw assembly. First and second longitudinal slots are defined between sides of the first and second arc portions and which extend from a top of the elongated arc portions to a bottom of the elongated arc portions. The two longitudinal slots are situated at diametrically opposite sides thereof. Each longitudinal slot aligns with a spinal rod slot of the spinal rod holder to thereby allow easy placement of the spinal rod into the spinal rod holder. Thereafter, the elongated arc portions provide direct communication and alignment with the top of the spinal rod holder by defining an elongated tube in order to receive a spinal rod holder drive screw for securing the spinal rod into the spinal rod holder. In this embodiment, the spinal rod guide is removed from the spinal rod holder after installation and securing of the spinal rod.

The present invention also provides a spinal rod guide assembly for mounting a spinal rod into a spinal rod holder of a vertebral bone screw assembly of the spinal rod guide assembly particularly, but not necessarily, for use in minimally invasive surgery. The spinal rod guide assembly includes a spinal rod guide that is initially attached to the spinal rod holder of the vertebral bone screw assembly. The spinal rod guide is configured to extend from an opening in a patient's body to the spinal rod connector, to receive a spinal rod therein, and thereafter accurately guide the spinal rod into the spinal rod connector. The spinal rod guide defines a guide tube for the introduction and placement of additional spinal rod components onto the spinal rod connector, particularly, but not necessarily, for securing the spinal rod into the spinal rod holder. The spinal rod guide is temporarily attached to the spinal rod connector in a manner that allows for easy detachment of the spinal rod guide from the spinal rod holder.

An embodiment of the spinal rod guide assembly includes a vertebral bone screw, a spinal rod holder pivotally coupled to the vertebral bone screw, and an elongated guide tube defined by first and second elongated arc portions that are attached onto a top of the spinal rod holder. The elongated guide tube has first and second longitudinal slots extending from a top of the elongated guide tube to a bottom of the elongated guide tube that align with first and second spinal rod slots of the spinal rod holder. The two longitudinal slots of the elongated guide tube and the two spinal slots of the spinal rod holder are situated at diametrically opposite sides. The slots allow easy placement of the spinal rod into the spinal rod holder. The elongated tube moreover provides direct communication and alignment with the top of the spinal rod holder in order to receive a spinal rod connector drive screw for securing the spinal rod into the spinal rod holder. The spinal rod guide is scored or otherwise connected at a junction between the spinal rod guide and the spinal rod holder such that the spinal rod guide is easily broken or snapped off from the spinal rod holder once installation of the spinal rod is complete.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 3 is a second side view of the spinal rod guide/guide assembly of FIG. 1 taken from a side of the spinal rod guide/guide assembly that is 90° from the side view of FIG. 2;

FIG. 4 is a sectional view of the spinal rod guide/guide assembly of FIG. 1 taken along line 4-4 of FIG. 3;

Like reference numerals indicate the same or similar parts throughout the several figures.

Figure 1:
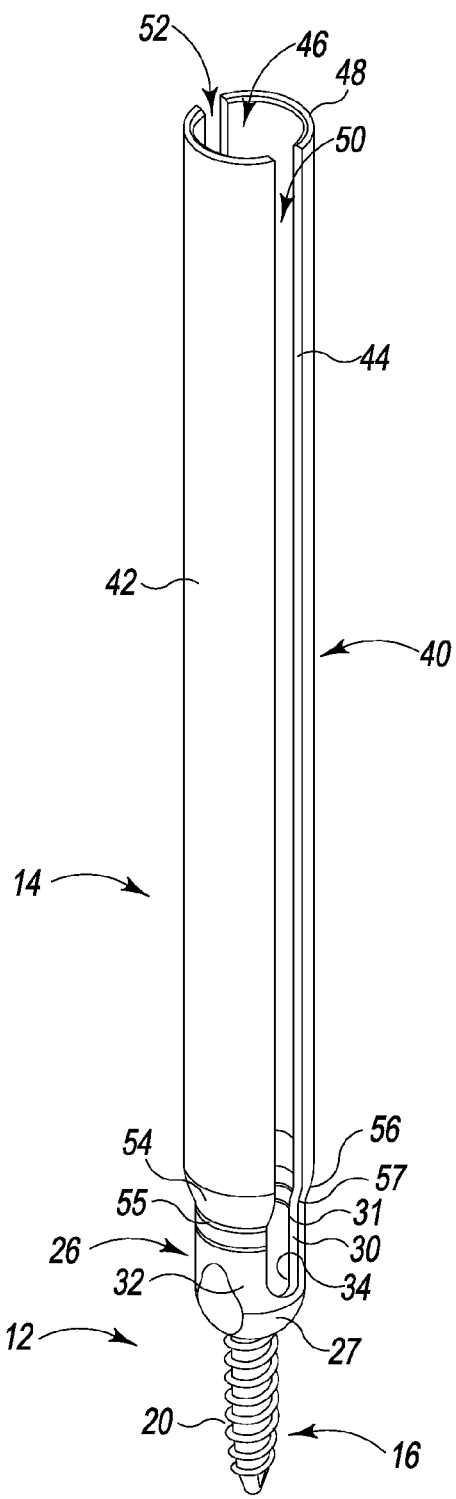
FIG. 1 is a side perspective view of an embodiment of a spinal rod guide/guide assembly in accordance with the principles of the present invention.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

FIGS. 1-6 depict various views of a spinal rod guide/guide assembly generally designated 10 for the introduction, placement and securing of a spinal rod relative to vertebrae of a patient. The spinal rod guide assembly 10 is defined by a vertebral bone screw assembly 12 that is particularly, but not necessarily, a pedicle bone screw assembly (pedicle screw assembly) 12 and a spinal rod guide component 14. The spinal rod guide 10 is defined by the spinal rod guide component 14. The spinal rod guide/guide assembly 10 is made from titanium, stainless steel or another biocompatible material.

In one form, the spinal rod guide 10 may be considered as the spinal rod guide component 14 and, as such, the terms are interchangeable. In another form, the spinal rod assembly 10 may be considered as the spinal rod guide component 14 and the pedicle bone screw assembly 12 and, as such, the terms are interchangeable.

The pedicle bone screw assembly 12 is formed of a pedicle screw 16 and a spinal rod holder or connector 18. The pedicle screw 16 is defined by a threaded body, shank or shaft 20 with a rounded head 22. A configured socket 24 is provided in the screw head 22. The spinal rod connector 18 is situated on the pedicle screw head 22. The spinal rod connector 18 and the pedicle screw head 22 are connected such that the spinal rod connector 18 can swivel or rotate about the pedicle screw head 22. This allows the spinal rod connector 18 to assume various orientations relative to the pedicle screw 16 in order to accommodate a spinal rod (not shown).

Figure 2:
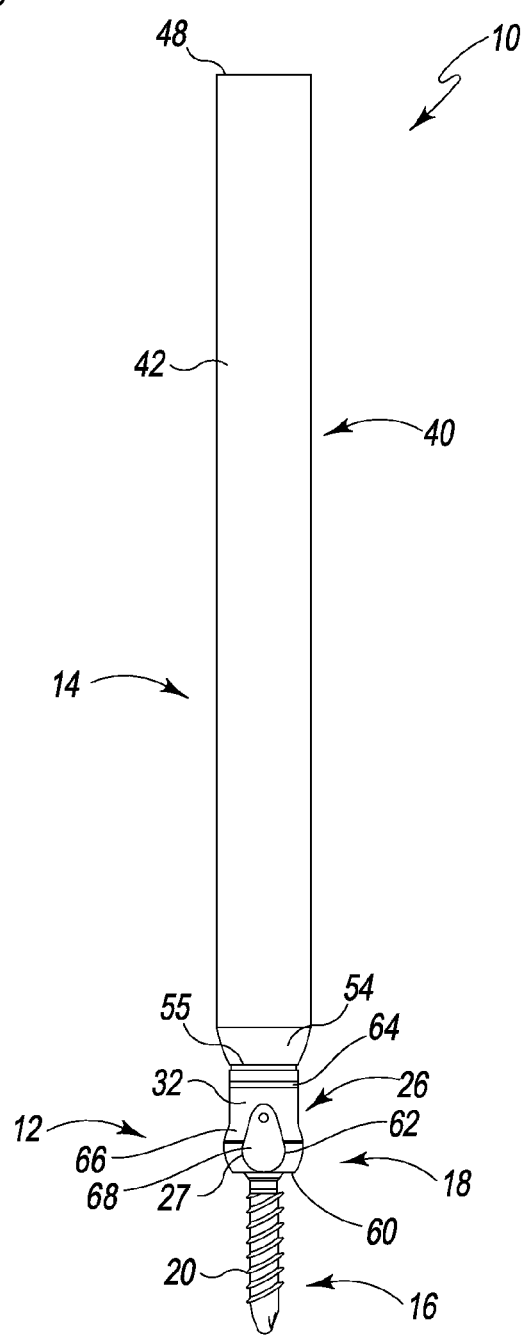
FIG. 2 is a side view of the spinal rod guide/guide assembly of FIG. 1.

The spinal rod connector 18 is defined by a generally tulip-shaped body 26 having a lower opening 28 that is configured to allow the pedicle screw shaft 20 to extend therethrough but to retain the pedicle screw head 22. The pedicle screw head 22 is thus sized to be rotatably captured by the body 26. Referring to FIG. 2 the curved tulip-shaped body 26 includes a lower (or first) end 60 where the opening 28 for the pedicle screw 16 is located, a middle portion 62, and an upper (or second) end 64 from which the first and second elongated arc portions 42, 44 extend from. Referring to FIGS. 2 and 3, the tulip shaped body 26 also includes an outer sidewall with a curved portion 66, a first cut-out portion 68, and a second cut out portion 70 located diametrically opposite the first cut-out portion 68. As shown in FIGS. 2 and 4, the curved outer sidewall at the middle portion 62 has a larger outer dimension than the curved outer sidewall at the first end 60 and the second end 64. The curved outer sidewall at the first end 60 has a larger outer dimension than the curved outer sidewall at the second end 64. By virtue of its shape, the body 26 has a first side or side member 30 and a second side or side member 32 extending from a base 27 of the body 26. The first and second side members 30 and 32 are separated from each other on one side by a first slot 34 and on another side by a second slot 36. The first and second side members 30 and 32 are essentially situated diametrically opposite one another on the body 26. The first and second slots 34 and 36 are likewise situated diametrically opposite one another on the body 26 and are sized and configured to receive a spinal rod therein (not shown). An upper inside surface of the first side member 30 includes threads 31, while an upper inside surface of the second side member 32 also includes threads 33. The threads 31, 32 are configured for receiving a threaded spinal rod connector screw (not shown) for securing the spinal rod (not shown) within the spinal rod connector 18.

The spinal rod guide component 14 is defined by a first elongated arc portion or side 42 and a second elongated arc portion or side 44 that together defined an elongated guide tube 40. The first and second elongated arc portions 42 and 44 are separated from one another on one side by a first elongated slot 50 and on another side by a second elongated slot 52. The first and second elongated arc portions 42 and 44 are essentially situated diametrically opposite one another on the guide tube 40. The first and second elongated slots 50 and 52 are likewise situated diametrically opposite one another on the guide tube 40 and are sized and configured to receive a spinal rod therein (not shown) and allow the spinal rod to slide down into the first and second slots 34 and 36 of the spinal rod connector 18. In this manner, a spinal rod (not shown) is guided from an upper end 48 of the tube into the spinal rod connector 18, and specifically into the first and second slots 34, 36 of the spinal rod connector 18, via the first and second elongated slots 50, 52.

The guide tube 40 moreover defines a tubular bore 46 that extends from the upper end 48 to the spinal rod holder body 26. The tubular bore 46 is sized to allow a pedicle screw driver to be received in the screw socket 24 and for a spinal rod holder screw (not shown) to be placed into the spinal rod connector 18 and be threadedly received by the first and second inner threads 31, 33 of the first and second sides 30. 32 of the spinal rod connector body 26 in order to secure a spinal rod (not shown) therein. Other components may also be placed through the guide tube 40.

Figure 5:
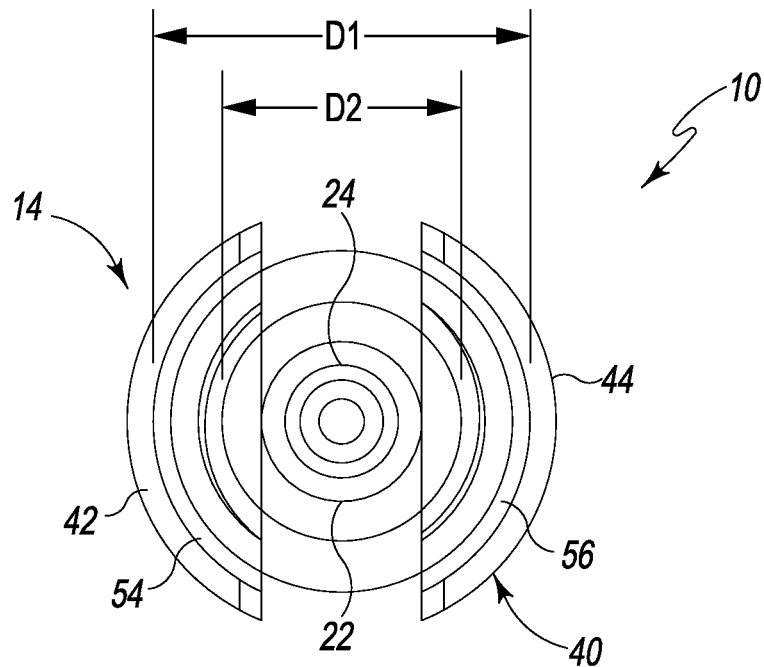
FIG. 5 is a top plan view of the spinal rod guide/guide assembly of FIG. 1 taken along line 5-5 of FIG. 3.
Figure 6:
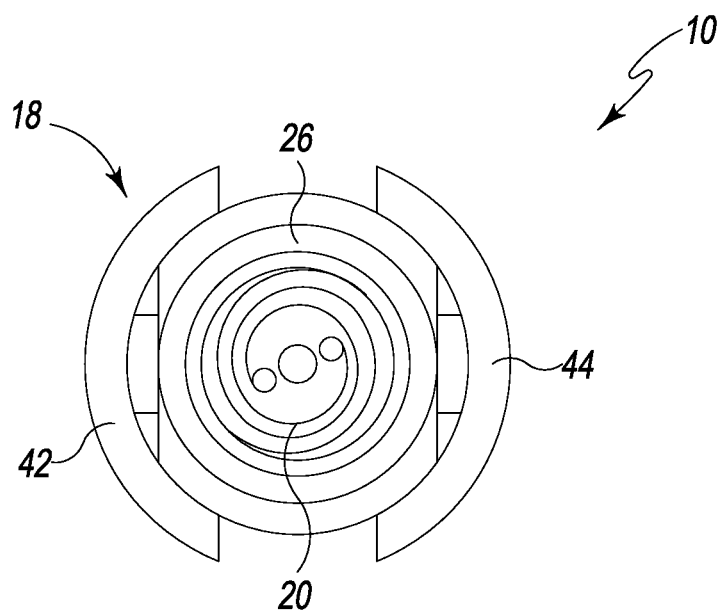
FIG. 6 is a bottom plan view of the spinal rod guide/guide assembly of FIG. 1 taken along line 6-6 of FIG. 3.

The spinal rod guide component 14 is shown having a first taper 54 on a lower end of the first elongated arc portion 42 of the guide tube 40 and a second taper 56 on a lower end of the second elongated arc portion 44 of the guide tube 40. It should be appreciated that such tapers are not necessary. Referring to FIG. 5, the first and second elongated arc portions define a guide tube having an inner diameter D1 that is greater than an inner diameter D2 of the spinal rod holder (see also FIG. 4 for comparison of relative dimensions). Referring to FIGS. 2 and 4, the first and second elongated arc portions have an outer diameter that is greater than an outer diameter of the spinal rod holder. Referring to FIG. 4, the first taper 54 and the second taper 56 have an outer diameter that is tapered and an inner diameter that is tapered. Referring to FIGS. 4 and 5, the first taper member 54 and the second taper member 56 define an inverted frustoconical bore.

In one embodiment, the spinal rod guide component 14 of the spinal rod guide assembly 10 and, more particularly, the guide tube 40 is formed with or made to the spinal rod holder 18. Particularly, the lower end of the first elongated arc portion 42 of the guide tube 40 is formed with or made to the second side 32 of the spinal rod holder body 26 while the lower end of the second elongated arc portion 44 of the guide tube 40 is formed with or made to the first side 30 of the spinal rod holder body 26. A first junction or juncture 55 is defined between the lower end of the first elongated arc portion 42 of the guide tube 40 and the second arc portion 32 of the spinal rod holder body 26. The first juncture 55 is scored or otherwise fashioned such that the first elongated arc portion 42 can break away or snap off from the second side 32. Likewise, a second junction or juncture 57 is defined between the lower end of the second elongated arc portion 44 of the guide tube 40 and the first side 30 of the spinal rod holder body 26. The second juncture 57 is scored or otherwise fashioned such that the second elongated arc portion 44 can break away or snap off from the first side 30. In this manner, when the spinal rod is set and secured in the spinal rod holder 18, the spinal rod guide component 14 may be removed.

In another embodiment, the spinal rod guide 14 may be attached or attachable to a spinal rod connector 18 by threads or another means. Particularly, the lower end of the first elongated arc portion 42 of the guide tube 40 may include threads that are threadedly received by threads on the second end 32 of the spinal rod holder body 26. Likewise, the lower end of the second elongated arc portion 44 of the guide tube 40 may include threads that are threadedly received by threads on the first end 30 of the spinal rod holder body 26. Thus, when the spinal rod is set and secured in the spinal rod holder 18, the spinal rod guide 14 may be threadedly removed from the spinal rod holder 18.

The inside surface, interior or inner lumen of the first and second arc portions (guide tube) may also include threads or threading along their (its) length. This allows a locking cap for the spinal rod holder to be threaded down the guide tube such that the locking cap pushes the spinal rod down into the spinal rod holder along with the locking cap to secure the spinal rod into the spinal rod holder. This also provides a manner to reduce a spondylolisthesis condition.

The present spinal rod guide/guide assembly allows easy installation of a spinal rod into one and/or a plurality of spinal rod connectors of pedicle screws and the fixing thereof utilizing a minimally invasive surgical technique.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. An apparatus for mounting a spinal rod to a vertebra, the apparatus comprising:
   a spinal rod holder having a base, a first side member extending from the base, and a second side member extending from the base, each of the first and second side members having a first end coupled to the base and a second end opposite the first end, the base having an opening sized to allow a pedicle screw to extend partially therethrough, the first and second side members separated by opposite first and second slots;
   a guide tube coupled to the spinal rod holder and configured to provide guided placement of the spinal rod into the spinal rod holder, the guide tube comprising:
     a first elongated arc member having a first end and a second end;
     a second elongated arc member having a first end and a second end;
     a first taper member connecting the first elongated arc member to the first side member, the first taper member having a first end and a second end;
     a second taper member connecting the second elongated arc member to the second side member, the second taper member having a first end and a second end;
     a first longitudinal slot defined by the first elongated arc member, the second elongated arc member, the first taper member, and the second taper member, the first longitudinal slot aligning with the first slot of the spinal rod holder; and
     a second longitudinal slot opposite the first longitudinal slot and defined by the first elongated arc member, the second elongated arc member, the first taper member, and the second taper member, the second longitudinal slot aligning with the second slot of the spinal rod holder;
     wherein the first ends of the first and second taper members are connected to the second ends of the first and second elongated arc members, and the second ends of the first and second taper members are connected to the second ends of the first and second side members of they spinal rod holder;
     wherein the first and second arc members define a guide bore having a first diameter, the first and second taper members define a tapered bore, and the first and second side members define a rod holder bore having a second diameter, wherein the first diameter is greater than the second diameter.

2. The apparatus of claim 1, wherein the first and second arc members are configured to extend from a vertebra to outside a patient's body.

3. The apparatus of claim 1, wherein the first and second longitudinal slots are situated diametrically opposite one another.

4. The apparatus of claim 1, wherein the guide tube has threading situated on an outer surface of a bottom thereof that is adapted to engage threads of the spinal rod holder.

5. The apparatus of claim 1, wherein:
   the first elongated arc member has first threads disposed along an inner lumen thereof; and
   the second elongated arc member has second threads disposed along an inner lumen thereof;
   the first and second threading adapted to allow internal threading of a spinal rod holder locking cap.

6. The apparatus of claim 1, wherein the first and second elongated arc members define the guide tube having an outer diameter that is greater than an outer diameter of the spinal rod holder.

7. The apparatus of claim 1, wherein the spinal rod holder includes a tulip-shaped body having a curved portion, a first cut-out portion, and a second cut-out portion located diametrically opposite the first cut-out portion, the curved portion of the tulip shaped body having a first end, a middle portion, and a second end, wherein the middle portion has a larger outer dimension than the first end and the second end.

8. The apparatus of claim 7, wherein the first end has a larger outer dimension than the second end.

9. The apparatus of claim 1, further comprising a first break juncture between the first taper member and the first side member, and a second break juncture between the second taper member and the second side member.

10. An apparatus for mounting a spinal rod to a vertebra, the apparatus comprising:
a spinal rod holder configured to pivotally receive a vertebral bone screw and having a base, first and second side members extending from the base, and first and second slots adapted to receive a spinal rod, the base having an opening sized to allow a pedicle screw to extend partially therethrough, the first and second side members defining a first outer diameter and a first inner diameter, each of the first and second side members having a first end coupled to the base and a second end opposite the first end;
a guide tube having a first elongated arc member, a second elongated arc member, a first taper member connecting the first elongated arc member to the first side member, and a second taper member connecting the second elongated arc member to the second side member, the first and second elongated arc members defining a second outer diameter and a second inner diameter, each of the first and second arc members having a first end and a second end, each of the first and second taper members having a first end and a second end;
a first longitudinal slot defined between the first elongated arc member, the second elongated arc member, the first taper member, and the second taper member, the first longitudinal slot aligning with the first slot of the spinal rod holder; and
a second longitudinal slot defined between the first elongated arc member, the second elongated arc member, the first taper member, and the second taper member, the second longitudinal slot aligning with the second slot of the spinal rod holder;
wherein the first outer diameter is greater than the second outer diameter and the first inner diameter is greater than the second inner diameter;
wherein the first ends of the first and second taper members are connected to the second ends of the first and second elongated arc members, and the second ends of the first and second taper members are connected to the second ends of the first and second side members of the spinal rod holder;
the first and second longitudinal slots providing guided placement of a spinal rod into the spinal rod holder.

11. The apparatus of claim 10, wherein the first and second arc members are configured to extend from a vertebra to outside a patient's body.

12. The apparatus of claim 10, wherein the first and second longitudinal slots are situated diametrically opposite one another.

13. The apparatus of claim 10, wherein the guide tube has threading situated on an outer surface of a bottom thereof that is adapted to engage threads of the spinal rod holder.

14. The apparatus of claim 13, wherein:
the first elongated arc portion has first threads disposed on an inner lumen thereof; and
the second elongated arc portion has second threads disposed on an inner lumen thereof;
the first and second threading adapted to allow internal threading of a spinal rod holder locking cap.

15. The apparatus of claim 10, wherein the guide tube is formed connected to the spinal rod holder and is adapted to be removed after installation of the spinal rod into the spinal rod holder.

16. The apparatus of claim 15, wherein the guide tube is scored at a junction between a bottom of the guide tube and a top of the spinal rod holder, whereby the guide tube may be broken off from the spinal rod holder.

17. The apparatus of claim 10, wherein the first taper member and the second taper member define an inverted frustoconical bore.

18. The apparatus of claim 10, wherein the spinal rod holder includes a curved tulip-shaped body, the tulip shaped body having a curved portion, the curved portion of the tulip shaped body having a lower end, a middle portion, and an upper end, wherein the middle portion has a larger outer dimension than the upper end, and wherein the upper end has a larger outer dimension than the lower end of the tulip-shaped body.

19. The apparatus of claim 18, wherein an outer dimension defined by the first and second elongated arc portions is larger than the diameter outer dimension of the second end of the tulip-shaped body.

20. The apparatus of claim 18, wherein the tulip-shaped body includes a first cut-out and a second cut-out portion, the first and second cut-out portions extending from proximate the lower end to between the middle portion and the upper end.

21. The apparatus of claim 10, further comprising a first break juncture between the first taper member and the first side member, and a second break juncture between the second taper member and the second side member.

22. A method for guiding a spinal rod into a spinal rod holder of a spinal rod bone screw assembly, the method comprising:
providing a spinal rod holder, a guide tube, and opposite first and second longitudinal slots, the spinal rod holder having a base, a first side member extending from the base, and a second side member extending from the base, the base having a lower end proximate an opening sized to allow a pedicle screw to extend partially therethrough, and a middle portion, the guide tube having a first elongated arc member, a second elongated arc member, a first taper member connecting a lower end of the first elongated arc member to an upper end of the first side member at a first break juncture, and a second taper member connecting a lower end of the second elongated arc member to an upper end of the second side member at a second break juncture, the first and second longitudinal slots defined by the first elongated arc member, the second elongated arc member, the first taper member, and the second taper member, wherein the first and second arc members define a guide bore having a first diameter, the first and second taper members define a tapered bore, and the first and second side members define a rod holder bore having a second diameter, wherein first diameter is greater than the second diameter;
placing a spinal rod into the first and second longitudinal slots; and sliding the spinal rod down the first and second longitudinal slots and into the spinal rod holder;

separating the first and second elongated arc portion from the rod holder at the first break juncture and the second break juncture.

23. A method for guiding a spinal rod into a spinal rod holder of a spinal rod bone screw assembly, the method comprising:

providing a spinal rod holder, a guide tube, and opposite first and second longitudinal slots, the spinal rod holder having a base and first and second side members extending from the base, the first and second side members defining a first outer diameter and a first inner diameter and having a first end connected to the base and a second end opposite the first end, the guide tube having a first elongated arc member, a second elongated arc member, a first taper member connecting an end of first elongated arc member to the second end of the first member, and a second taper member connecting an end of the second elongated arc member to the second end of the second member, the first and second longitudinal slots defined by the first elongated arc member, the second elongated arc member, the first taper member, and the second taper member, the first and second elongated arc members defining a second outer diameter and a second inner diameter, wherein the first outer diameter is greater than the second outer diameter and the first inner diameter is greater than the second inner diameter, and wherein the first and second taper members define a tapered bore;

placing a spinal rod into the first longitudinal slot, parallel to the axis created by the elongated arc portions; and sliding the spinal rod down the first longitudinal slot and angling the rod into the second longitudinal slot as it is slid downward; and sliding the spinal rod down the first and second longitudinal slots and the tapered bore into the spinal rod holder.

* * * * *